United States Patent [19]
Wulff-Döring et al.

[11] Patent Number: 6,057,442
[45] Date of Patent: May 2, 2000

[54] PREPARATION OF AMINES

[75] Inventors: Joachim Wulff-Döring, Frankenthal; Michael Hesse, Worms; Johann-Peter Melder, Neuhofen; Philipp Buskens, Hoogstraten; Guido Voit, Freinsheim; Frank Funke, Limburgerhof, all of Germany

[73] Assignee: BASF Aktiengesellschaft, Ludwigshafen, Germany

[21] Appl. No.: 09/159,089

[22] Filed: Sep. 23, 1998

[30] Foreign Application Priority Data

Sep. 29, 1997 [DE] Germany ............... 197 42 911

[51] Int. Cl.⁷ .................................. C07C 209/16
[52] U.S. Cl. ............... 544/106; 564/347; 564/349; 564/480; 502/324; 502/327
[58] Field of Search .................. 502/324, 327; 564/347, 349, 480; 544/106

[56] References Cited

U.S. PATENT DOCUMENTS

| | | |
|---|---|---|
| 4,014,933 | 3/1977 | Boetter et al. . |
| 4,151,204 | 4/1979 | Ichikawa et al. . |
| 5,002,922 | 3/1991 | Irgang et al. . |
| 5,166,433 | 11/1992 | Irgang et al. . |
| 5,530,127 | 6/1996 | Reif et al. . |
| 5,608,113 | 3/1997 | Becke et al. . |

FOREIGN PATENT DOCUMENTS

| | | |
|---|---|---|
| 382 049 | 8/1990 | European Pat. Off. . |
| 254 335 | 1/1992 | European Pat. Off. . |
| 514 692 | 11/1992 | European Pat. Off. . |
| 696 572 | 2/1996 | European Pat. Off. . |
| 697 395 | 2/1996 | European Pat. Off. . |
| 1 953 263 | 2/1972 | Germany . |

*Primary Examiner*—Samuel Barts
*Attorney, Agent, or Firm*—Keil & Weinkauf

[57] ABSTRACT

Amines are prepared from primary or secondary alcohols and nitrogen compounds selected from the group of ammonia, primary and secondary amines, at from 80 to 250° C. under pressures from 0.1 to 40 MPa with hydrogen in the presence of a catalyst comprising zirconium, copper and nickel, wherein the catalytically active composition comprises 20–85% by weight of oxygen-containing zirconium compounds, calculated as $ZrO_2$, 1–30% by weight of oxygen-containing copper compounds, calculated as $CuO$, 14–70% by weight of oxygen-containing nickel compounds, calculated as $NiO$, where the molar ratio of nickel to copper is greater than 1, 0–10% by weight of oxygen-containing aluminum and/or manganese compounds, calculated as $Al_2O_3$ and/or $MnO_2$, and no oxygen-containing cobalt or molybdenum compounds.

9 Claims, No Drawings

PREPARATION OF AMINES

The preparation of amines

The present invention relates to a process for preparing amines from primary or secondary alcohols and nitrogen compounds selected from the group of ammonia, primary and secondary amines, at from 80 to 250° C. under pressures from 0.1 to 40 MPa with hydrogen in the presence of a catalyst comprising zirconium, copper and nickel.

DE-A-19 53 263 discloses the preparation of amines by reductive amination of the corresponding alcohols on catalysts comprising cobalt, nickel and copper. Alumina or silica is used as carrier material in these catalysts. Good conversions can be achieved with these catalysts at high temperatures and pressures, but the conversion and the selectivity decrease greatly at lower temperatures and pressures.

EP-A-254 335 discloses Ni-Co-Ru catalysts on alumina or silica carriers which additionally comprise halides in their active composition for the reductive amination of alcohols. The maximum conversions achieved with these catalysts are only 61%.

U.S. Pat. No. 4,151,204 discloses catalysts for preparing amino alcohols which consist of a metal such as cobalt, nickel or copper, preferably of nickel or cobalt, and may be doped with small amounts of zirconium, adding the zirconium in a molar ratio of from 0.005:1 to 0.2:1 relative to nickel or cobalt. Larger zirconium contents lead to side reactions such as decomposition of the products.

EP-A-382 049 discloses catalysts and processes for reductive amination of alcohols. Although these catalysts, whose active composition comprises oxygen-containing zirconium, copper, cobalt and nickel compounds, have good activity and selectivity, their useful lives are in need of improvement.

EP-A-696 572 and EP-A-697 395 disclose catalysts comprising nickel, copper, zirconium oxide and molybdenum oxide for the catalytic amination of alcohols with nitrogen compounds and hydrogen. Although high conversions are achieved with these catalysts, byproducts are formed (eg. ethylamine) and themselves, and secondary products thereof, interfere with the workup.

EP-A-514 692 discloses catalysts comprising copper, nickel and/or cobalt, zirconium oxide and/or aluminum oxide for the catalytic amination of alcohols in the gas phase with ammonia or primary amines and hydrogen. This application discloses that the atomic ratio of nickel to copper in these catalysts must be from 0.1 to 1.0, preferably from 0.2 to 0.5 (compare loc. cit., Example 1), otherwise increased amounts of byproducts, which reduce the yield, occur on amination of alcohols (loc. cit., Examples 6 and 12). The carrier which is preferably used is alumina (loc. cit., Examples 1 to 5 and 7 to 11).

It is an object of the present invention to remedy the abovementioned disadvantages.

We have found that this object is achieved by an improved process for preparing amines from primary or secondary alcohols and nitrogen compounds selected from the group of ammonia, primary and secondary amines, at from 80 to 250° C. under pressures from 1 to 400 bar with hydrogen in the presence of a zirconium, copper and nickel catalyst, wherein the catalytically active composition comprises 20–85% by weight of oxygen-containing zirconium compounds, calculated as $ZrO_2$, 1–30% by weight of oxygen-containing copper compounds, calculated as CuO, 14–70% by weight of oxygen-containing nickel compounds, calculated as NiO, where the molar ratio of nickel to copper is greater than 1, 0–10% by weight of oxygen-containing aluminum and/or manganese compounds, calculated as $Al_2O_3$ and/or $MnO_2$, and no oxygen-containing cobalt or molybdenum compounds.

The catalysts according to the invention are preferably employed in the form of unsupported catalysts. The term unsupported catalyst indicates that, in contrast to a supported catalyst, the catalyst consists only of catalytically active composition. Unsupported catalysts can be employed by introducing the catalytically active composition, which has been ground to a powder, into the reaction vessel, or by the catalytically active composition being ground, mixed with molding aids, molded and heat-treated and then being disposed as catalyst moldings, eg. as beads, cylinders, rings, coils, in the reactor.

The concentration data, in each case calculated as $ZrO_2$, NiO, CuO, $Al_2O_3$ and $MnO_2$ after the last heat treatment of the catalyst and before its reduction with hydrogen are based in each case, unless indicated otherwise, on the catalytically active composition of the catalyst. The catalytically active composition of the catalyst is defined as the total of the masses of the catalytically active constituents and comprises essentially the catalytically active constituents zirconium, nickel, copper, and optionally aluminum and/or manganese.

The total of the catalytically active constituents calculated as $ZrO_2$, NiO, CuO, $Al_2O_3$ and $MnO_2$ is usually 70 to 100% by weight, preferably 80 to 100% by weight, particularly preferably 90 to 100% by weight, very particularly preferably 100% by weight.

The zirconium oxide content of the catalysts according to the invention is generally from 20 to 85% by weight, preferably 25 to 50% by weight.

The content of oxygen-containing aluminum and/or manganese compounds, calculated as $Al_2O_3$ and/or $MnO_2$, in the catalytically active composition can be up to 10% by weight, with the ratio by weight of zirconium, calculated as $ZrO_2$, to aluminum and/or manganese, calculated as $Al_2O_3$ and/or $MnO_2$, being at least 2.

The other components, calculated as nickel oxide and copper oxide, are generally present in total amounts of from 15 to 80% by weight, preferably 50 to 75% by weight, in the catalytically active composition, with the molar ratio of nickel to copper being greater than 1.

The catalysts contain in their catalytically active composition

20–85% by weight, preferably 25–50% by weight, of oxygen-containing zirconium compounds, 1–30% by weight, preferably 10–25% by weight, of oxygen-containing copper compounds, 14–70% by weight, preferably 40–60% by weight, of oxygen-containing nickel compounds, where the molar ratio of nickel to copper is greater than 1, preferably greater than 1.2, particularly preferably from 2 to 6, and 0–10% by weight of oxygen-containing aluminum and/or manganese compounds, where the ratio by weight of zirconium, calculated as $ZrO_2$, to aluminum and/or manganese, calculated as $Al_2O_3$ and/or $MnO_2$, is preferably at least 5.

Particularly preferred catalysts are those containing no oxygen-containing aluminum and/or manganese compounds.

Various procedures are possible for preparing the unsupported catalysts. They can be obtained, for example, by peptizing powdered mixtures of the hydroxides, carbonates, oxides and/or other salts of the components zirconium, nickel and copper with water and subsequently extruding and heat-treating the resulting composition.

However, precipitation methods are generally used to prepare the catalysts according to the invention. Thus, they can be obtained, for example, by joint precipitation of the nickel and copper components from an aqueous salt solution containing these elements using mineral bases in the presence of a suspension of an oxygen-containing zirconium compound of low solubility, and subsequently washing, drying and calcining the resulting precipitate. Examples of oxygen-containing zirconium compounds of low solubility which can be used are zirconium dioxide, zirconium oxide hydrate, zirconium phosphates, borates and silicates. The suspensions of the zirconium compounds of low solubility can be prepared by suspending fine powders of these compounds in water with vigorous stirring. The suspensions are advantageously obtained by precipitating the zirconium compounds of low solubility from aqueous zirconium salt solutions using mineral bases.

The catalysts according to the invention are preferably prepared by joint precipitation (mixed precipitation) of all their components. This is expediently done by adding an aqueous mineral base, in particular an alkali metal base, for example sodium carbonate, sodium hydroxide, potassium carbonate or potassium hydroxide, to a hot aqueous salt solution containing the catalyst components with stirring until the precipitation is complete. The nature of the salts used is not generally critical: since what principally matters in this procedure is the solubility of the salts in water, one criterion for the preparation of these relatively highly concentrated salt solutions is that they necessarily have good solubility in water. It is regarded as self-evident that, in the selection of the salts of the individual components, of course the anions in the salts chosen will not result in interference, whether by causing unwanted precipitation or by impeding or preventing the precipitation through complex formation.

The precipitates obtained in these precipitation reactions are generally chemically inhomogeneous and consist inter alia of mixtures of the oxides, oxide hydrates, hydroxides, carbonates and insoluble and basic salts of said metals. It may prove to be beneficial for the filterability of the precipitates for them to be aged, i.e. to be left alone for some time after the precipitation, where appropriate with heating or passing air through.

The precipitates obtained by these precipitation processes are further processed to the catalysts according to the invention in a conventional way. After washing, they are generally dried at from 80 to 200° C., preferably at 100 to 150° C., and then calcined. The calcination is generally carried out at from 300 to 800° C., preferably at from 400 to 600° C., in particular at from 450 to 550° C.

After the calcination, the catalyst is expediently conditioned, whether by adjusting to a particular particle size by grinding, or by being ground and then mixed with molding aids such as graphite or stearic acid, compressed to moldings in a tabletting press and heat-treated. The temperatures for this heat treatment generally correspond to those for the calcination.

The catalysts prepared in this way contain the catalytically active metals in the form of a mixture of their oxygen-containing compounds, i.e. in particular as oxides and mixed oxides.

The catalysts prepared in this way are stored and, where appropriate, marketed as such. They are normally reduced before being used as catalysts for the reductive amination of alcohols. However, they can also be employed without prior reduction, in which case they are reduced by the hydrogen present in the reactor under the conditions of the reductive amination. For the prior reduction, the catalysts are generally first exposed to a nitrogen/hydrogen atmosphere at from 150 to 200° C. for a period of from 12 to 20 hours and then treated in a hydrogen atmosphere at from 200 to 400° C. for up to about 24 hours. In this prior reduction, some of the oxygen-containing metal compounds present in the catalysts are reduced to the corresponding metals, so that they are present together with the various types of oxygen compounds in the active form of the catalyst.

Amines of the formula I

where $R^1$ and $R^2$ are hydrogen, $C_1$–$C_{20}$-alkyl, $C_3$–$C_{12}$-cycloalkyl, aryl, $C_7$–$C_{20}$-aralkyl and $C_7$–$C_{20}$-alkylaryl or together $(CH_2)_l$—X—$(CH_2)_m$, $R^3$ and $R^4$ are hydrogen, alkyl such as $C_1$–$C_{200}$-alkyl-, cycloalkyl such as $C_3$–$C_{12}$-cycloalkyl, $C_1$–$C_{20}$-hydroxyalkyl, amino- and/or hydroxyl-substituted $C_1$–$C_{20}$-alkyl, alkoxyalkyl such as $C_2$–$C_{30}$-alkoxyalkyl, dialkylaminoalkyl such as $C_3$–$C_{30}$-dialkylaminoalkyl, alkylaminoalkyl such as $C_2$–$C_{30}$-alkylaminoalkyl, $R^5$-$(OCR^6R^7CR^8R^9)_n$-, -$(OCR^6R^7)$, aryl, hetaryl, aralkyl such as $C_7$–$C_{20}$-aralkyl, hetarylalkyl such as $C_4$–$C_{20}$-hetarylalkyl, alkylaryl such as $C_7$–$C_{20}$-alkylaryl, alkylhetaryl such as $C_4$–$C_{20}$ alkylhetaryl and Y—$(CH_2)$m—$NR^5$—$(CH_2)_q$ or together $(CH_2)_l$—X—$(CH_2)_m$ or $R^2$ and $R^4$ are together $(CH_2)_l$—X—$(CH_2)_m$, $R^5$, $R^{10}$ are hydrogen, $C_1$–$C_4$-alkyl, $C_{12}$–$C_{40}$-alkylphenyl, $R^6$, $R^7$, $R^8$, $R^9$ are hydrogen, methyl or ethyl, x is $CH_2$, oxygen or N—$R^5$, Y is $N(R^{10})_2$, hydroxyl, $C_2$–$C_{20}$-alkylaminoalkyl or $C_3$–$C_{20}$-dialkylaminoalkyl, n is an integer from 1 to 30, l, m, q are an integer from 1 to 4, are of particular commercial interest. The process according to the invention is therefore preferably used for these amines, in which case primary or secondary alcohols of the formula II

$$R^4—CHR^3—OH \qquad (II),$$

are reacted with nitrogen compounds of the formula III

where $R^1$ and $R^2$, and $R^3$ and $R^4$, have the abovementioned meanings.

The substituents $R^1$, $R^2$, $R^3$, $R^4$, $R^5$, $R^6$, $R^7$, $R^8$, $R^9$, $R^{10}$ and the indices l, m and n in the compounds I, II and III have the following meanings, independently of one another:

$R^1$, $R^2$, $R^3$, $R^4$, $R^5$, $R^6$, $R^7$, $R^8$, $R^9$, $R^{10}$
  hydrogen, $R^3$, $R^4$ $C_1$–$C_{200}$-alkyl, preferably $C_1$–$C_8$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, 2-ethylhexyl, n-decyl, 2-n-propyl-n-heptyl, n-tridecyl, 2-n-butyl-n-nonyl and 3-n-butyl-n-nonyl, particularly preferably isopropyl, 2-ethylhexyl, n-decyl, 2-n-propyl-n-heptyl, n-tridecyl, 2-n-butyl-n-nonyl and 3-n-butyl-n-nonyl, and preferably $C_{40}$–$C_{200}$-alkyl such as polybutyl, polyisobutyl, polypropyl, polyisopropyl and polyethyl, particularly preferably polybutyl and polyisobutyl, $R^1$ and $R^2$ or $R^3$ and $R^4$ or $R^2$ and $R^4$ together a —$(CH_2)_l$—X—$(CH_2)_m$- group, $R^1$, $R^2$, $R^3$, $R^4$ $C_3$–$C_{12}$-cycloalkyl, preferably $C_3$–$C_8$-cycloalkyl such as cyclopropyl, cyclobutyl, cyclopentyl, cyclohexyl, cycloheptyl and cyclooctyl, particularly preferably cyclopentyl, cyclohexyl and cyclooctyl, aryl, such as phenyl, 1-naphthyl, 2-naphthyl, 1-anthryl, 2-anthryl and 9-anthryl, preferably phenyl, 1-naphthyl and 2-naphthyl, particularly preferably phenyl, $C_7$–$C_{20}$-alkylaryl, preferably $C_7$–$C_{12}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl, $C_7$–$C_{20}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl, $R^1$, $R^2$ $C_1$–$C_{20}$-alkyl, preferably $C_1$–$C_8$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, particularly preferably $C_1$–$C_8$-alkyl such as methyl, ethyl, n-propyl, isopropyl, n-butyl, isobutyl, sec-butyl and tert-butyl, $R^3$, $R^4$ $C_1$–$C_{20}$-hydroxyalkyl, preferably $C_1$–$C_8$-hydroxyalkyl, particularly preferably $C_1$–$C_4$-hydroxyalkyl such as hydroxymethyl, 1-hydroxyethyl, 2-hydroxyethyl, 1-hydroxy-n-propyl, 2-hydroxy-n-propyl, 3-hydroxy-n-propyl and 1-hydroxy-methyl-ethyl, amino- and hydroxyl-substituted $C_1$–$C_{20}$-alkyl, preferably amino- and/or hydroxyl-substituted $C_1$–$C_8$-alkyl, particularly preferably amino and/or hydroxyl-substituted $C_1$–$C_4$-alkyl such as N-(hydroxyethyl)aminoethyl and N-(aminoethyl)aminoethyl, $C_2$–$C_{30}$-alkoxyalkyl, preferably $C_2$–$C_{20}$-alkoxyalkyl, particularly preferably $C_2$–$C_8$-alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl, particularly preferably $C_2$–$C_4$-alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl, $R^5$-$(OCR^6R^7CR^8R^9)_n$-$(OCR^6R^7)$, preferably $R^5$-$(OCHR^7CHR^9)_n$-$(OCR^6R_7)$, particularly preferably $R^5$-$(OCH_2CHR^9)_n$-$(OCR^6R^7)$, $C_3$–$C_{30}$-dialkylaminoalkyl, preferably $C_3$–$C_{20}$-dialkylaminoalkyl, particularly preferably $C_3$–$C_{10}$-dialkylaminoalkyl such as dimethylaminomethyl, dimethylaminoethyl, diethylaminoethyl, di-n-propylaminoethyl and diisopropylaminoethyl, $(R^5)_2N$-$(CH_2)_q$, $C_2$–$C_{30}$-alkylaminoalkyl, preferably $C_2$–$C_{20}$-alkylaminoalkyl, particularly preferably $C_2$–$C_8$-alkylaminoalkyl such as methylaminomethyl, methylaminoethyl, ethylaminomethyl, ethylaminoethyl and iso-propylaminoethyl, $(R^5)HN$-$(CH_2)_q$, Y-$(CH_2)_m$—$NR^5$—$(CH_2)_q$, $C_4$–$C_{20}$-hetarylalkyl, such as 2-pyridylmethyl, 2-furanyl-methyl, 3-pyrrolylmethyl and 2-imidazolylmethyl, $C_4$–$C_{20}$-alkylhetaryl such as 2-methyl-3-pyridinyl, 4,5-dimethyl-2-imidazolyl, 3-methyl-2-furanyl and 5-methyl-2-pyrazinyl, hetaryl, such as 2-pyridinyl, 3-pyridinyl, 4-pyridinyl, pyrazinyl, 3-pyrrolyl, 2-imidazolyl, 2-furanyl and 3-furanyl, $R^5$, $R^{10}$ $C_1$–$C_4$-alkyl such as methyl, ethyl, n-propyl, isopropyl, n-butyl, isobutyl, sec-butyl and tert-butyl, preferably methyl and ethyl, particularly preferably methyl, $C_{12}$–$C_{40}$-alkylphenyl, preferably $C_{14}$–$C_{40}$-alkylphenyl such as 2-, 3-, 4-nonylphenyl, 2-, 3-, 4-decylphenyl, 2,3-, 2,4-, 2,5-, 3,4-, 3,5-dinonylphenyl, 2,3-, 2,4-, 2,5-, 3,4- and 3,5-didecylphenyl, $R^6$, $R^7$, $R^8$, $R^9$ methyl and ethyl, preferably methyl,

X $CH_2$, oxygen or N-$R^5$,

Y $N(R^{10})_2$, hydroxyl, $C_2$–$C_{20}$-alkylaminoalkyl, preferably $C_2$–$C_{16}$-alkylaminoalkyl such as methylaminomethyl, methylaminoethyl, ethylaminomethyl, ethylaminoethyl and isopropylaminoethyl, $C_3$–$C_{20}$-dialkylaminoalkyl, preferably $C_3$–$C_{16}$-dialkylaminoalkyl such as dimethylaminomethyl, dimethylaminoethyl, diethylaminoethyl, di-n-propylaminoethyl and diisopropylaminoethyl, l an integer from 1 to 4 such as 1, 2, 3 and 4, preferably 2 and 3, particularly preferably 2, m, q an integer from 1 to 4 such as 1, 2, 3 and 4, preferably 2, 3 and 4, particularly preferably 2 and 3, n an integer from 1 to 10, preferably an integer from 1 to 8 such as 1, 2, 3, 4, 5, 6, 7 or 8, particularly preferably an integer from 1 to 6 such as 1, 2, 3, 4, 5 or 6.

Suitable alcohols are virtually all primary and secondary aliphatic alcohols. The aliphatic alcohols may be straight-chain, branched or cyclic. Secondary alcohols are aminated just as well as primary alcohols. There are virtually no limits on the number of carbons in the alcohols which can be aminated. The alcohols may furthermore have substituents which are inert under the conditions of the reductive amination, for example alkoxy, alkyleneoxy or alkylamino groups. If polyhydric alcohols are to be aminated, it is possible to obtain amino alcohols, cyclic amines or polyaminated products by controlling the reaction conditions. Amination of 1,5-diols results, depending on the chosen reaction conditions, in 1-amino-5-hydroxy, 1,5-diamino compounds or six-membered rings with one nitrogen atom. Accordingly from diglycol it is possible to obtain monoaminodiglycol (=ADG=$H_2N$—$CH_2CH_2$—O—$CH_2CH_2$—OH), diaminodiglycol or, particularly preferably, morpholine. Correspondingly, piperazine is particularly preferably obtained from diethanolamine. N-(2-hydroxyethyl) piperazine can be obtained from triethanolamine.

Examples of alcohols which are preferably aminated are the following:

Methanol, ethanol, n-propanol, isopropanol, n-butanol, isobutanol, n-pentanol, n-hexanol, 2-ethylhexanol, tridecanol, stearyl alcohol, palmityl alcohol, cyclopentanol, cyclohexanol, ethanolamine, n-propanolamine, isopropanolamine, n-pentanolamine, n-hexanolamine, diethanolamine, N-alkyldiethanolamines, diisopropanolamine, N,N-dimethylaminoethanol, N,N-diethylaminoethanol, N,N-di-n-propylaminoethanol, N,N-diisopropylaminoethanol, N,N-di-n-butylaminoethanol, N,N-diisobutylaminoethanol, N,N-di-sec-butylaminoethanol, N,N-di-tert-butylaminoethanol, N,N-dimethylaminopropanol, N,N-diethylaminopropanol, N,N-di-n-propylaminopropanol, N,N-diisopropylaminopropanol, N,N-di-n-butylaminopropanol, N,N-diisobutylaminopropanol, N,N-di-sec-butylaminopropanol, N,N-di-tert-butylaminopropanol, 1-dimethylamino-4-pentanol, 1-diethylamino-4-pentanol, ethylene glycol, 1,2-propylene glycol, 1,3-propylene glycol, diglycol, 1,4-butanediol, 1,5-pentanediol, 1,6-hexanediol, 2,2-bis[4-hydroxycyclohexyl]propane, methoxyethanol, propoxyethanol, butoxyethanol, polyisobutyl alcohols, polypropyl alcohols, polyethylene glycol ethers, polypropylene glycol ethers and polybutylene glycol ethers. The last-mentioned polyalkylene glycol ethers are converted in the reaction according to the invention into the corresponding amines by conversion of their free hydroxyl groups.

Aminating agents which can be employed in the reductive amination of alcohols are both ammonia and primary or secondary, aliphatic or cycloaliphatic amines.

When ammonia is used as aminating agent, the alcoholic hydroxyl groups are converted first into free amino groups (—$NH_2$). The primary amines formed in this way are able to react with further alcohol to give the corresponding secondary amines, and these in turn are able to react with further alcohol to give the corresponding symmetrical tertiary amines. It is thus possible to prepare, as required, preferably primary, secondary or tertiary amines depending on the composition of the reaction mixture and depending on the reaction conditions used-pressure, temperature, reaction time.

It is possible in this way to prepare from polyhydric alcohols, by intramolecular reductive amination, cyclic amines such as pyrrolidines or piperidines, piperazines and morpholines.

Primary or secondary amines can be used just as well as ammonia as aminating agents.

These aminating agents are preferably used to prepare nonsymmetrically substituted di- or trialkylamines such as ethyl diisopropylamine and ethyl dicyclohexylamine. Examples of mono- and dialkylamines preferably used as aminating agents are the following: methylamine, dimethylamine, ethylamine, diethylamine, propylamine, diisopropylamine, butylamine, pentylamine, hexylamine and cyclohexylamine.

The aminating agent can be employed in stoichiometric amount relative to the alcoholic hydroxyl group to be aminated. However, the aminating agent is preferably used in excess, generally with a more than 5-molar excess per mole of alcoholic hydroxyl group to be aminated. Ammonia in particular is generally employed in a 1.5 to 250-fold, preferably 5 to 100-fold, in particular 10 to 80-fold, molar excess per mole of alcoholic hydroxyl groups to be reacted. Larger excesses both of ammonia and of primary or secondary amines are possible.

The hydrogen is fed into the reaction generally in an amount of from 5 to 400 l, preferably in an amount of from 50 to 200 l, per mole of alcohol component, the stated liters having been converted to standard temperature and pressure (S.T.P.) in each case.

The reaction is generally carried out without additional solvent. When reacting high molecular weight starting compounds or products which are highly viscous or solid at room temperature, it may be advantageous also to use a solvent which is inert under the reaction conditions, such as tetrahydrofuran, dioxane, N-methylpyrrolidone or ethylene glycol dimethyl ether.

The reaction is normally carried out at from 80 to 300° C., preferably from 120 to 230° C., particularly preferably from 130 to 220° C. The reaction is generally carried out at a pressure of from 0.1 to 40 MPa. However, pressures of from 1 to 25 MPa, in particular from 3 to 22 MPa, are preferably used.

It is possible to use higher temperatures and a higher overall pressure. The overall pressure in the reaction vessel, which is composed of the total of the partial pressures of the aminating agent, of the alcohol component and of the products formed in the reaction and, where appropriate, of the solvent which is present at the stated temperatures, is expediently adjusted by injecting hydrogen to give the required reaction pressure.

It may be advantageous for the selectivity of the present process to mix the catalyst moldings with inert packing elements in the reactor, as it were to dilute them. The proportion of the packing elements in such catalyst preparations can be from 20 to 80, in particular 30 to 60 and especially 40 to 50, parts by volume.

The practical procedure is generally such that the alcohol and the aminating agent are fed simultaneously into the catalyst, which is normally present in a fixed bed reactor, which is preferably externally heated, at the required reaction temperature under the required pressure. The space velocity is generally from 0.02 to 3, preferably 0.05 to 2, and particularly preferably 0.1 to 1.6, l of alcohol per liter of catalyst an hour. In this connection, it is expedient to heat the reactants before feeding them into the reaction vessel, preferably to the reaction temperature.

The reactor can be operated in either an upflow or a downflow manner, ie. the reactants can be passed either from the bottom to the top or else from the top to the bottom through the reactor. It is self-evident that the process can be carried out both batchwise and continuously. In both cases, the excess aminating agent can be recycled together with the hydrogen. If the conversion in the reaction is incomplete, the unreacted starting material can likewise be returned to the reaction zone.

After the reaction discharge has expediently been decompressed, the excess aminating agent and the hydrogen are removed from it, and the resulting amination products are purified by distillation, liquid extraction or crystallization. The excess aminating agent and the hydrogen are advantageously returned to the reaction zone. The same applies to any unreacted or incompletely reacted alcohol component.

The water formed during the reaction generally does not adversely affect the conversion, the reaction rate, the selectivity and the useful life of the catalyst, and is therefore expediently removed from the reaction product only when the latter is worked up by distillation.

The amines obtainable according to the invention are suitable inter alia as intermediates for preparing fuel additives (U.S. Pat. No. 3,275,554; DE-A-21 25 039 and DE-A-36 11 230), surfactants, drugs and crop protection agents, and vulcanization accelerators.

EXAMPLES

A. Preparation of Catalysts

Preparation of Catalyst A (according to the invention)

An aqueous solution of nickel nitrate, copper nitrate and zirconium acetate, which contained 4.48% NiO, 1.52% CuO and 2.82% $ZrO_2$, was simultaneously precipitated in a stirred vessel at a constant flow rate with a 20% strength aqueous sodium carbonate solution at 70° C. in such a way that the pH, measured with a glass electrode, was maintained at 7.0.

The resulting suspension was filtered, and the filter cake was washed with deionized water until the electrical conductivity of the filtrate was about 20 mS. The filter cake was then dried at 150° C. in a drying oven or a spray dryer. The hydroxide/carbonate mixture obtained in this way was then heat-treated at 500° C. for 4 hours.

The catalyst A obtained in this way had the composition:

51% by weight Ni, calculated as NiO,

17% by weight Cu, calculated as CuO,

32% by weight Zr, calculated as $ZrO_2$.

The catalyst powder was mixed with 3% by weight graphite and shaped to 5×3 mm tablets.

Preparation of Catalyst B (for comparative test in accordance with DE-A-1 953 263)

Alumina extrudates with a diameter of 4 mm were covered with a solution containing 5% by weight each of Co and Ni and 2% by weight of Cu (calculated as metal). This solution contained the metal nitrates.

After impregnation for about 15 minutes, the extrudates were dried at 120° C. and then heat-treated at 520° C.

The impregnation/drying/heat treatment were then repeated. The resulting catalyst B had the composition:

76% by weight Al, calculated as $Al_2O_3$,

4% by weight Cu, calculated as CuO,

10% by weight Co, calculated as CoO,

10% by weight Ni, calculated as NiO.

Preparation of Catalyst C (for comparative test in accordance with EP-A-382 049)

A catalyst C was prepared for comparative tests on the basis of EP-A-382 049 as follows: A solution of zirconium, copper(II), cobalt(II) and nickel(II) salts was pumped at the same time as sodium carbonate solution with a density of 1.208 kg/l into a precipitation apparatus which contained freshly precipitated zirconium dioxide suspended in water. The pH of the solution was kept constant at 6.0 during the precipitation, and was raised to pH 7.5 after the consumption of the mineral salt solution. The precipitate was washed, dried to constant weight at 120° C. and calcined to constant weight at 400° C. The resulting crude catalyst composition was ground, mixed with 3% by weight graphite, tabletted and calcined once again at 520° C. for 3 hours.

The resulting catalyst C had the composition:

76% by weight Zr, calculated as $ZrO_2$,

4% by weight Cu, calculated as CuO,

10% by weight Co, calculated as CoO,

10% by weight Ni, calculated as NiO.

Preparation of Catalyst D (for comparative test in accordance with EP 696 572)

The catalyst was prepared as for catalyst A but, after the washing, ammonium heptamolybdate was incorporated, as described on page 8 of EP-A-696 572, into the still moist filter cake so that the resulting catalyst D had the following composition.

50% by weight Ni, calculated as NiO,

17% by weight Cu, calculated as CuO, 1.5% by weight Mo, calculated as $MoO_3$, 31.5% by weight Zr, calculated as $ZrO_2$.

The catalyst powder was mixed with 3% by weight graphite and shaped to 5×3 mm tablets.

B. Preparation of Morpholine by Reductive Amination of Diglycol

Example 1 According to the Invention

A continuously operated high-pressure reactor was packed with 500 cm³ of Catalyst A, and 270 cm³ of diglycol and 500 cm³ of liquid ammonia were passed in per hour. The catalyst temperature was adjusted to 180° C., and the pressure in the reactor was adjusted to 200 bar by simultaneously injecting hydrogen. Excess ammonia was distilled out of the reaction discharge after it had been decompressed. Analysis of the collected reaction discharges by gas chromatography revealed the following composition:

Morpholine: 29%

Aminodiglycol: 26%

Diglycol: 40%

Ethylamine: 1400 ppm

Other compounds incl. water: <5%

The morpholine selectivity was 48%.

Example 2 Comparative Example

When the test described in Example 1 was carried out using catalyst B, it was necessary to adjust the temperature to 220° C., with the reaction conditions otherwise identical to those of Example 1, in order to achieve comparable diglycol conversion. Analysis of the collected reaction discharges by gas chromatography revealed the following composition:

Morpholine: 17%

Aminodiglycol: 37%

Diglycol: 42%

Other compounds incl. water: 4%

The morpholine selectivity was 29%.

Catalyst B was thus distinctly less reactive, because the required reaction temperature was higher, than catalyst A according to the invention, and it also showed a considerably lower morpholine selectivity.

Example 3 Comparative Example

When the test described in Example 1 was carried out using catalyst C, it was necessary to adjust the temperature to 185° C., with the reaction conditions otherwise identical to those of Example 1, in order to achieve comparable diglycol conversion. Analysis of the collected reaction discharges by gas chromatography revealed the following composition:

Morpholine: 27%

Aminodiglycol: 31%

Diglycol: 36%

Other compounds incl. water: 6%

The morpholine selectivity was 42%.

This catalyst had decomposed after the test had lasted a few days and was therefore unsuitable.

Example 4 Comparative Example

When the test described in Example 1 was carried out using catalyst D, it was necessary to adjust the temperature to 190° C., with the reaction conditions otherwise identical to those of Example 1, in order to achieve comparable diglycol conversion. Analysis of the collected reaction discharges by gas chromatography revealed the following composition:

Morpholine: 21%

Aminodiglycol: 30%

Diglycol: 43%

Ethylamine: 5200 ppm

Other compounds incl. water: <6%

The morpholine selectivity was 37%.

Catalyst D showed a considerably lower morpholine selectivity for the reaction and, furthermore, a distinctly more pronounced formation of the interfering ethylamine than did catalyst A according to the invention in Example 1.

We claim:

1. A process for preparing amines from primary or secondary alcohols and nitrogen compounds selected from the group of ammonia, primary and secondary amines, at from 80 to 250° C. under pressures from 0.1 to 40 MPa with hydrogen in the presence of a catalyst comprising zirconium, copper and nickel, wherein the catalytically active composition comprises 20–85% by weight of oxygen-containing zirconium compounds, calculated as $ZrO_2$, 1–30% by weight of oxygen-containing copper compounds, calculated as CuO, 14–70% by weight of oxygen-containing nickel compounds, calculated as NiO, where the molar ratio of nickel to copper is greater than 1, 0–10% by weight of oxygen-containing aluminum and/or manganese compounds, calculated as $Al_2O_3$ and/or $MnO_2$, and no oxygen-containing cobalt or molybdenum compounds.

2. A process as claimed in claim 1, wherein when an aluminum and/or manganese oxygen compound is present the ratio by weight of zirconium, calculated as $ZrO_2$, to aluminum and/or manganese, calculated as $Al_2O_3$ and/or $MnO_2$, is at least 5.

3. A process as claimed in claim 1, wherein the catalytically active composition comprises 25–50% by weight of oxygen-containing zirconium compounds, calculated as $ZrO_2$, 10–25% by weight of oxygen-containing copper compounds, calculated as CuO, and 40–60% by weight of oxygen-containing nickel compounds, calculated as NiO, where the molar ratio of nickel to copper is greater than 1.

4. A process as claimed in claim 1 for preparing amines of the formula I

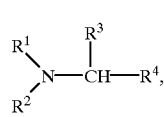
(I)

where $R^1$ and $R^2$ are hydrogen, $C_1$–$C_{20}$-alkyl, $C_3$–$C_{12}$-cycloalkyl, aryl, $C_7$–$C_{20}$-aralkyl and $C_7$–$C_{20}$-alkylaryl or together $(CH_2)_l$—X—$(CH_2)_m$, $R^3$ and $R^4$ are hydrogen, alkyl, cycloalkyl, hydroxyalkyl, amino- and/or hydroxyl-substituted alkyl, alkoxyalkyl, dialkylaminoalkyl, alkylaminoalkyl, $R^5$-$(OCR^6R^7CR^8R^9)_n$-$(OCR^6R^7)$, aryl, hetaryl, aralkyl, hetarylalkyl, alkylaryl, alkylhetaryl and Y—$(CH_2)_m$—$NR^5$—$(CH_2)_q$ or together $(CH_2)_l$—X—$(CH_2)_m$ or $R^2$ and $R^4$ are together $(CH_2)_l$—X—$(CH_2)_m$, $R^5$, $R^{10}$ are hydrogen, $C_1$–$C_4$-alkyl, $C_{12}$–$C_{40}$-alkylphenyl, $R^6$, $R^7$, $R^8$, $R^9$ are hydrogen, methyl or ethyl, X is $CH_2$, oxygen or N—$R^5$, Y is $N(R^{10})_2$, hydroxyl, $C_2$–$C_{20}$-alkylaminoalkyl or $C_3$–$C_{20}$-dialkylaminoalkyl, n is an integer from 1 to 30, l, m, q are an integer from 1 to 4, from primary or secondary alcohols of the formula II $$R^4\text{---}CHR^3\text{---}OH \qquad (II),$$

and nitrogen compounds of the formula III

(III)

5. A process as claimed in claim 1, wherein the reaction is carried out at from 120 to 230° C.

6. A process as claimed in claim 1, wherein the reaction is carried out under pressures of from 1 to 25 MPa.

7. A process as claimed in claim 1, wherein the reaction is carried out under pressures of from 3 to 22 MPa.

8. A catalyst, the catalytically active composition of which comprises

20–85% by weight of oxygen-containing zirconium compounds, calculated as $ZrO_2$, 1–30% by weight of oxygen-containing copper compounds, calculated as CuO, 14–70% by weight of oxygen-containing nickel compounds, calculated as NiO, where the molar ratio of nickel to copper is greater than 1, 0–10% by weight of oxygen-containing aluminum and/or manganese compounds, calculated as $Al_2O_3$ and/or $MnO_2$, and no oxygen-containing cobalt or molybdenum compounds.

9. A catalyst as claimed in claim 8, the catalytically active composition of which comprises 25–50% by weight of oxygen-containing zirconium compounds, calculated as $ZrO_2$, 10–25% by weight of oxygen-containing copper compounds, calculated as CuO, 40–60% by weight of oxygen-containing nickel compounds, calculated as NiO, where the molar ratio of nickel to copper is greater than 1, 0–10% by weight of oxygen-containing aluminum and/or manganese compounds, calculated as $Al_2O_3$ and/or $MnO_2$, and no oxygen-containing cobalt or molybdenum compounds.

* * * * *